(12) United States Patent
Wechter

(10) Patent No.: US 7,932,076 B2
(45) Date of Patent: *Apr. 26, 2011

(54) COMPOSITIONS FOR CULTURING SPIROCHETES

(75) Inventor: Stephen R. Wechter, Alpha, OH (US)

(73) Assignee: Stephen R. Wechter, Alpha, OH (US)

( * ) Notice: Subject to any disclaimer, the term of this patent is extended or adjusted under 35 U.S.C. 154(b) by 12 days.

This patent is subject to a terminal disclaimer.

(21) Appl. No.: 11/768,408

(22) Filed: Jun. 26, 2007

(65) Prior Publication Data

US 2009/0053796 A1    Feb. 26, 2009

Related U.S. Application Data

(63) Continuation of application No. 09/550,025, filed on Apr. 14, 2000, now Pat. No. 7,235,397.

(51) Int. Cl.
*C12N 1/20* (2006.01)

(52) U.S. Cl. ..................... 435/253.6; 435/243

(58) Field of Classification Search .......... None
See application file for complete search history.

(56) References Cited

U.S. PATENT DOCUMENTS

| | | | |
|---|---|---|---|
| 4,464,470 A * | 8/1984 | Fieldsteel et al. ......... 435/252.1 |
| 4,540,564 A | 9/1985 | Bodor |
| 4,638,043 A | 1/1987 | Szycher |
| 4,771,059 A | 9/1988 | Bodor |
| 4,824,850 A | 4/1989 | Bodor |
| 5,112,596 A | 5/1992 | Malfroy-Camine |
| 5,154,924 A | 10/1992 | Friden |
| 5,187,065 A | 2/1993 | Schutzer |
| 5,260,210 A | 11/1993 | Rubin |
| 5,264,360 A * | 11/1993 | Riviere ..................... 435/252.1 |
| 5,268,164 A | 12/1993 | Kozarich |
| 5,296,483 A | 3/1994 | Bodor |
| 5,506,206 A | 4/1996 | Kozarich |
| 5,643,561 A | 7/1997 | Katsuen |
| 5,643,602 A | 7/1997 | Ulmius |
| 5,686,416 A | 11/1997 | Kozarich |
| 5,752,515 A | 5/1998 | Jolesz |
| 5,792,110 A | 8/1998 | Cunningham |
| 5,830,505 A | 11/1998 | Fischer |
| 5,834,016 A | 11/1998 | Naeff |
| 5,876,746 A | 3/1999 | Jona |
| 7,235,397 B1 * | 6/2007 | Wechter ..................... 435/256.8 |

FOREIGN PATENT DOCUMENTS

WO    WO 99/24613    5/1999

OTHER PUBLICATIONS

Mikx et al. (Infection and Immunity, 1992, vol. 90, pp. 1761-1766).*
Koneman et al., "Color Atlas and Textbook of Diagnostic Microbiology," Fourth Edition, p. 762.
Kersten, et al. "Effects of Penicillin, Ceftriaxone, and Doxycycline on Morphology of Borrelia burgdorferi" Antimicrobial Agents and Chemotherapy. May 1995, vol. 39, No. 5, pp. 1127-1133.
Mikx, et al. "Hemagglutination Activity of Treponema denticola Grown in Serum-Free Medium in Continuous Culture" Infection and Immunity. May 1992, vol. 60, No. 5, pp. 1761-1766.
Waites, et al. "Direct Susceptibility Testing with Positive BacT/Alert Blood Cultures by using MicroScan Overnight and Rapid Panels" Journal of Clinical Microbiology. Jul. 1998, vol. 36, No. 7, pp. 2052-2056.

* cited by examiner

*Primary Examiner* — Robert A Zeman
(74) *Attorney, Agent, or Firm* — Casimir Jones, S.C.

(57) ABSTRACT

The present invention relates to methods and compositions for culturing spirochetes and treating spirochetal diseases. For example, the present invention provides serum-free media for culturing spirochete bacteria in vitro. The present invention further provides methods for identifying spirochete susceptibilities to antimicrobials and antimicrobial compositions and cocktails. The present invention also provides methods for treating subjects suspected of having a spirochete infection.

5 Claims, 1 Drawing Sheet

FIGURE 1

```
  1  NCGGNCAAGTACGATCTAATTAGCAACAGTAGACAAGCTTGAGCAAAGGAACTTCCGATAAAAACAATGGATCTGGAGTA
 81  CTTGAAGGCGTAAAAGCTGACAAAAGTAAAGTAAAATTAACAATTTCTGACGATCTAGGTCAAACCACACTTGAAGTTTT
161  CAAAGAAGATGGCAAAACACTAGTATCAAAAAAAGTAACTTCCAAAGACAAGTCATCAACAGAAGAAAAATTCAATGAAA
241  AAGGTGAAGTATCTGAAAAAATAATAACAAGAGCAGACGGAACCAGACTTGAATACACAGGAATTAAAAGCGATGGATAC
321  AANNN
```

Sequenced Fragment of *B. Burgdorferi* Outer Surface Protein A From Patient Sample

SEQUENCE LISTING

```
<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
aaaatgttag cagccttgac g                                              21

<210> SEQ ID NO 2
<211> LENGTH: 28
```

```
-continued
<212> TYPE: DNA
<213> ORGANISM: Artificial Sequence
<220> FEATURE:
<223> OTHER INFORMATION: Synthetic

<400> SEQUENCE: 2
agatccatcg cttttaattc ctgtgtat                                          28

<210> SEQ ID NO 3
<211> LENGTH: 325
<212> TYPE: DNA
<213> ORGANISM: Borrelia burgdorferi
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (323)..(325)
<223> OTHER INFORMATION: n is a, c, g, or t

<400> SEQUENCE: 3
ncggncaagt acgatctaat tagcaacagt agacaagctt gagcaaagga acttccgata        60
aaaacaatgg atctggagta cttgaaggcg taaaagctga caaaagtaaa gtaaaattaa       120
caatttctga cgatctaggt caaaccacac ttgaagtttt caagaagat ggcaaaacac        180 tagtatcaaa aaaagtaact tccaaagaca agtcatcaac agaagaaaaa ttcaatgaaa       240
aaggtgaagt atctgaaaaa ataataacaa gagcagacgg aaccagactt gaatacacag       300
gaattaaaag cgatggatac aannn                                             325
```

COMPOSITIONS FOR CULTURING SPIROCHETES

This application is a Continuation of U.S. application Ser. No. 09/550,025 filed Apr. 14, 2000, now U.S. Pat. No. 7,235,397 issued on Jun. 26, 2007 which is incorporated herein by reference in its entirety.

FIELD OF THE INVENTION

The present invention relates to methods and compositions for culturing spirochetes and treating spirochetal diseases. For example, the present invention provides serum-free media for culturing spirochete bacteria in vitro. The present invention further provides methods for identifying spirochete susceptibilities to antimicrobials and antimicrobial compositions and cocktails. The present invention also provides methods for treating subjects suspected of having a spirochete infection.

BACKGROUND OF THE INVENTION

Members of the Order Spirochaetales include organisms responsible for diseases associated with significant morbidity and mortality in humans and other animals. The spirochetes are helically shaped, motile bacteria that stain as Gram negative, and include the genera *Borrelia, Brachyspira, Cristipira, Leptonema, Leptospira, Serpulina, Spirochaeta, Treponema, Pillotina, Diplocalyx, Hollandina,* and *Clevelandina*. Of these genera, the *Borrelia, Leptospira,* and *Treponema* are responsible for the majority of human disease.

The Spirochetes

The genus *Borrelia* includes numerous species, the most clinically significant of which is *B. burgdorferi*, the etiologic agent of Lyme disease. Other *Borrelia* are historically significant as causative agents of epidemics, including *B. recurrentis* (synonyms include *B. obermeyeri* and *B. novyi*), *B. duttoni, B. hermisii*, and various others. For example, during the first half of the 1900s, more than 50 million people contracted louse-borne relapsing fever, with epidemics occurring throughout Europe, Africa, Asia, and South America (Schwan et al., *Borrelia*, in Murray (ed.), *Manual of Clinical Microbiology*, American Society for Microbiology, Washington, D.C. [1995], pages 626-635). Since 1959, more than 840 cases, including at least 6 deaths have been recorded from Jordan, Rwanda and Iran (See, Schwan et al, supra).

The genus *Leptospira* includes pathogenic as well as non-pathogenic serovars, although the pathogenicity is not a criterion for species differentiation. Nonetheless, the pathogenic serovars have been traditionally included within the species *L. interrogans* and the free-living non-pathogenic serovars have been included within the species *L. biflexa*. Over 210 serovars of *L. interrogans* and 63 serovars of *L. biflexa* have been officially described (Kaufmann and Weyant, *Leptospiraceae*, in Murray (ed.), *Manual of Clinical Microbiology*, American Society for Microbiology, Washington, D.C. [1995], pages 621-625). Leptospirosis is a zoonotic disease, with reservoirs in wild, domestic and feral animals. The disease can be very serious in humans and other animals, most notably pinnipeds. In humans, it is characterized by a biphasic illness in which about 10% of patients develop icteric leptospirosis. Icteric leptospirosis can be clinically severe, with a mortality rate of approximately 10% (See, Kaufmann and Weyant, supra).

The genus *Treponema* includes four human pathogens and at least six species that are not human pathogens. The most clinically significant species is *T. pallidum*, which includes three subspecies. *T. pallidum* subsp. *pallidum* is the etiologic agent of venereal syphilis, while *T. pallidum* subsp. *pertenue* is the etiologic agent of yaws (frambesia, pian), and *T. pallidum* subsp. *endemicum* is the etiologic agent of endemic syphilis (bejel, dichuchwa). *T. carateum*, the etiologic agent of pinta (carate, cute) represents the fourth pathogenic organism within this genus. Despite the availability of effective therapy, venereal syphilis remains an important sexually transmitted disease with a worldwide distribution. For example, in the United States, 112,581 cases were reported in 1992, which included 33,973 cases of primary and secondary syphilis and 3,850 cases of congenital syphilis (Norris and Larsen, *Treponema and Other Host-Associated Spirochetes* Murray (ed.), *Manual of Clinical Microbiology*, American Society for Microbiology, Washington, D.C. [1995], pages 636-651). Although venereal syphilis is of greatest concern in the United States, the other forms of treponemal disease are significant in terms of morbidity and mortality worldwide. Endemic syphilis is restricted to the desert and temperate regions of North Africa and the Middle East, while yaws occurs most frequently in the tropical and desert regions of Africa, South America, and Indonesia, and pinta is primarily observed in tropical areas of Central and South America (Norris and Larsen, supra). Yaws, endemic syphilis and pinta were endemic in certain areas prior to the establishment of eradication programs by the World Health Organization. In the 1950s, it was estimated that 200 million people were exposed to these diseases (Norris and Larsen, supra).

Cultivation and Identification of Spirochetes

In general, the spirochetes are difficult to culture and some have a requirement for in vivo cultivation methods. Indeed, Lyme disease spirochetes are difficult to detect in human patients. However, *Borrelia* can be cultivated either in their arthropod vectors or in a large variety of vertebrate hosts, although cultivation in embryonated chicken eggs is also possible. In vitro cultivation of *Borrelia* is most often done using Barbour-Stoenner-Kelly II (BSK II) medium, pH 7, with incubation in a microaerophilic environment at 30° to 37° C. The culture medium is monitored for spirochetes by dark field microscopy for 4 to 6 weeks. Traditionally, cultivation is conducted in the presence of gelatin and rabbit serum, as it has been reported that many months of incubation may be required to successfully grow these organisms in the absence of these components (See, Schwan et al., supra). An additional consideration is that continuous serial passages, even over a short period may effect many biological changes in the organisms, altering the phenotypic and genotypic characteristics.

Historically, identification of the *Borrelia* heavily depended upon the geographic distribution and natural arthropod vectors. The development of molecular diagnostic procedures has greatly enhanced the ability to identify these organisms, although direct identification of *B. burgdorferi* in clinical material by polymerase chain reaction (PCR) has proven unreliable, except in cases where synovial fluid is used (See, Schwann et al., supra). Serologic confirmation of borrelioses is often attempted using methods such as immunofluorescence (IFA) and enzyme immunoassays (ELISA or EIA), and Western blots. In addition, molecular identification methods have been developed.

Disease caused by leptospires is often presumptively diagnosed based on direct detection of organisms in a sample. These methods require skill and experience in order to correctly differentiate organisms from artifacts in the samples. In vitro methods have also been developed to cultivate leptospires. However, their fastidious nature makes this a complicated and time-consuming undertaking. Most often, semi-solid medium such as Fletcher's, Ellinghausen's, or polysorbate 80 is used. Traditionally, leptospiral cultures are maintained at room temperature, and cultures are observed once a week, for at least five weeks, using dark field microscopy. Before reporting a culture as "negative," the culture is examined twice a month for four months. Once grown in culture, leptospires can be identified to serogroup by the microscopic agglutination test (MAT). Other serologic methods have also been developed (e.g., indirect hemagglutination, slide agglutination, and ELISA), although none of these alternative methods appear to have the necessary sensitivity and specificity for clinical diagnostics (See, Kaufmann and Weyant).

The *Treponema* present even greater challenges to the microbiologist, as the *T. pallidum* subspecies and *T. carateum* are obligate human parasites, with no known non-human animal or environmental reservoirs. Thus, diagnosis of such diseases as syphilis is based on direct microscopic examination of material collected from lesions, non-treponemal tests (for screening), and treponemal tests (for confirmation). The criteria for syphilis diagnosis are divided into three categories, namely definitive, presumptive, and suggestive. The Treponemes are reported as noncultivatable in vitro. In the United States, the routine testing scheme is direct microscopic examination of lesion exudates, followed by a non-treponemal test, which is then confirmed with a treponemal test, if positive (See, Norris and Larsen). The diagnosis of other treponemal diseases is even more cumbersome, as no laboratory methods have been developed to distinguish the other pathogenic treponematoses from each other or from syphilis. Indeed, the standard serologic tests for syphilis are uniformly reactive with yaws, pinta, and endemic syphilis (See, Norris and Larsen). Thus, diagnosis of these diseases can be problematic.

Treatment of Spirochetal Diseases

For borrelial infections, there appears to be general agreement that antibiotics are preferable to the arsenical compounds traditionally used to treat these diseases. For Lyme disease, treatment regimens depend upon the nature and severity of the clinical manifestations. Very few prospective randomized therapeutic trials have been conducted, and MICs (minimum inhibitory concentrations) and MBCs (minimum bactericidal concentrations) are inconsistently reported in the literature.

For leptospires, standardized procedures have yet to be developed for antimicrobial susceptibility testing (See, Kaufmann and Weyant). However, in vitro testing has demonstrated strain variability in the susceptibility of the organisms to penicillin and tetracyclines. Indeed, additional methods need to be developed before in vitro testing of leptospires can be recommended for selection of treatment regimens. Furthermore, the limited availability of laboratories with the requisite capabilities for leptospiral disease diagnostics remains a problem worldwide.

In the United States, the Centers for Disease Control (CDC) publish recommended guidelines for the treatment of syphilis. Treatment of syphilis is often empirical, as antimicrobial testing is not straightforward (i.e., due to the lack of a method for continuous culture of *T. pallidum*). Various approaches been developed to determine the susceptibilities of representative strains (e.g., Nichols strain) to antimicrobial agents based on criteria such as the in vitro loss of mobility or infectivity, treatment of experimental animal infections, human trials, and examination of non-pathogenic cultivable treponemes.

SUMMARY

In sum, methods and compositions are needed for the reliable cultivation, detection, identification, and treatment of spirochetal disease. The currently used methods are very cumbersome, time-consuming, and require a high level of skill and experience to perform. The need for improved methods and compositions is highlighted by the increase in diseases associated with spirochetes.

Furthermore, the lack of reliable, easy to use culturing methods also has led to an unfortunate lack of information regarding the many disease states that may have an underlying spirochete component, and that may be treated with antibiotics specific for the spirochete. What is needed are reliable methods for culturing all spirochetes. The art is also in need of effective treatments for spirochete infections and methods for detecting spirochete infection and detecting diseases associated with spirochete infection.

SUMMARY OF THE INVENTION

The present invention relates to methods and compositions for culturing spirochetes and treating spirochetal diseases. For example, the present invention provides serum-free media for culturing spirochete bacteria in vitro. The present invention further provides methods for identifying spirochete susceptibilities to antimicrobials and antimicrobial compositions and cocktails. The present invention also provides methods for treating subjects suspected of having a spirochete infection.

The present invention provides a composition comprising culture media capable of growing *Treponema* organisms in vitro. In some embodiments of the present invention the composition is capable of growing *Treponema* organisms in vitro under microaerophilic conditions (i.e., under conditions containing oxygen, but at a lower than atmospheric concentrations). In other embodiments of the present invention, the composition is capable of growing *Treponema* organisms in vitro under anaerobic conditions (i.e., absence of oxygen). In some embodiments, the composition further comprising a dividing population of *Treponema* organism. In preferred embodiments, the *Treponema* organisms comprise *Treponema pallidum*. In some embodiments, the culture media is serum-free culture media.

The present invention also provides a composition comprising serum-free culture media capable of growing *Treponema*, *Borrelia*, and *Leptospira* organisms (i.e., capable of growing each of the organisms). In some embodiments of the present invention, the serum-free culture media is capable of growing *Treponema*, *Borrelia*, and *Leptospira* organisms in vitro. In some embodiments, the composition further comprises a dividing population of a spirochete organism.

The present invention further provides methods for detecting spirochetes in a sample comprising providing: a sample suspected of containing at least one genus of spirochete organism, and serum-free culture media capable of growing *Treponema*, *Borrelia*, and *Leptospira* organisms in vitro; inoculating the culture media with the sample; culturing the sample in the culture media to produce an expanded culture; and detecting the presence of the spirochete organisms in the expanded culture. The present invention is not limited to any particular sample type. In some embodiments, the sample is selected from a water sample, an animal sample, an insect sample, and a fluid sample. In preferred embodiments, the animal sample comprises a tissue or fluid. In preferred embodiments, the animal sample comprises a human sample. In particularly preferred embodiments, the human sample comprises a sample from a patient suspected of having a neurological or autoimmune disease. For example, in some embodiments, the human sample comprises a sample from a patient having symptoms of a disease selected from multiple sclerosis and rheumatoid arthritis. In preferred embodiments, the spirochete organisms is selected from *Treponema, Borrelia*, and *Leptospira*.

The present invention also provides a method for determining antimicrobial susceptibility of spirochete organisms, comprising providing: a sample suspected of having a spirochete organism, culture media capable of growing *Treponema, Borrelia*, and *Leptospira* organisms in vitro; and one or more antimicrobial agents; culturing the sample in the culture media to produce an expanded culture; treating the expanded culture with the one or more antimicrobial agents; and determining the susceptibility of the spirochete organisms in the expanded culture to the one or more antimicrobial agents. In preferred embodiments, the spirochete organisms is selected from *Treponema, Borrelia*, and *Leptospira*. In some embodiments, the one or more antimicrobial agents comprise antibiotics. In some embodiments, the sample comprises a sample from a human patient, wherein the method further comprises the steps of selecting one or more antimicrobials that kill the spirochetes; and treating the human patient with the one or more antimicrobials that kill the spirochetes.

In yet other embodiments, the further comprising the step of selecting one or more antimicrobials that kill said spirochetes. The present invention further provides an antimicrobial composition comprising at least one antimicrobial agent selected using the above methods.

The present invention also provides an antimicrobial composition containing one or more antimicrobial agents selected using a method comprising: providing a plurality of samples containing at least one spirochete organism; conducting an in vitro antimicrobial susceptibility assay on the plurality of samples; and selecting one or more antimicrobial agents collectively capable of killing spirochetes in at least 80% of said samples. In preferred embodiments, the antimicrobial agents are collectively capable of killing spirochetes in at least 90% of the samples, more preferably at least 95% of the samples, and most preferably at least 99% of the samples.

The present invention further provides an antispirochete antimicrobial composition comprising a tetracycline antibiotic and a quinalone antibiotic.

The present invention also provides a method of treating a subject having symptoms of multiple sclerosis comprising: providing a subject having symptoms of multiple sclerosis; and treating the subject with any of the above antimicrobial compositions.

The present invention further provides a method of treating a subject having symptoms of rheumatoid arthritis comprising: providing a subject having symptoms of rheumatoid arthritis; and treating the subject with any of the above antimicrobial compositions.

The present invention also provides a method of treating a subject suspected of having a spirochetal infection comprising treating the subject with any of the above antimicrobial compositions.

The present invention further provides a method of treating a subject having symptoms of multiple sclerosis comprising: providing a subject with symptoms of multiple sclerosis; and a composition comprising a tetracycline antibiotic and a quinalone antibiotic; and administering the composition to the subject. In some embodiments, the tetracycline antibiotic is minocycline and the quinalone antibiotic is ciprofloxacin.

DESCRIPTION OF THE FIGURES

FIG. 1 presents a sequence fragment of *B. burdorferi* surface protein A from a human patient sample.

GENERAL DESCRIPTION OF THE INVENTION

The present invention relates to methods and compositions for culturing spirochetes and treating spirochetal diseases. For example, the present invention provides serum-free media for culturing spirochete bacteria in vitro. The present invention further provides methods for identifying spirochete susceptibilities to antimicrobials (e.g., antibiotics) and antimicrobial compositions and cocktails. The present invention also provides methods for treating subjects suspected of having a spirochete infection.

For example, the present invention provides methods and media for culturing spirochetes. In some embodiments of the present invention, the media is a defined, serum-free media for culturing any and all spirochete species in vitro. The methods and media of the present invention represent the first reliable serum-free media for culturing spirochetes and provide the only in vitro method available for culturing Treponemes. Thus, the present invention provides powerful new systems for culturing spirochetes, allowing spirochete detection and characterization.

The present invention also provides methods and compositions for spirochete detection. For example, in some embodiments of the present invention, samples suspected of containing at least one spirochete species or subspecies are cultured in the media of the present invention to produce a sufficient number of organisms to permit their ready detection. It is contemplated that samples from any source will be used in the implementation of the present invention. For example, environmental samples (e.g., water, soil, etc.), as well as clinical and veterinary samples will be used in conjunction with the present invention. Indeed, it is contemplated that spirochetal transmission will also be assessed using the present invention (e.g., the use of cord blood to detect maternal transmission of organisms to the fetus in utero).

Importantly, the methods and compositions of the present invention facilitate determinations regarding the role of spirochetes in particular disease states or patient symptoms, including diseases not currently associated with a spirochete etiology. For example, the present invention demonstrates an association between spirochetal infection and the presentation of patient symptoms and diagnosis of diseases such as multiple sclerosis, arthritis, as well as other diseases (e.g., neurological and autoimmune diseases).

The present invention also provides methods and compositions for conducting antimicrobial susceptibilities, including methods and compositions suitable for use in testing spirochetes for which no methods are currently available. In one embodiment of the present invention, the media of the present invention is used to culture a sufficient amount of spirochete organism to allow treatment with one or more antimicrobials (e.g., in an antimicrobial cocktail). Thus, these methods identify antimicrobials that may be used to decontaminate a sample (e.g., a water sample) or to treat subjects infected with a spirochete. These methods of the present invention also allow for the identification of antimicrobials or antimicrobial cocktails specific to a certain patient or class of patients and allow for the identification of antimicrobials or antimicrobial cocktails that are statistically most likely to successfully treat diseases due to any spirochete.

Thus, in some embodiments, the present invention provides methods and compositions for treating patients infected with spirochetes and/or patients suspected of experiencing spirochete infection (e.g., patients exhibiting symptoms or disease states associated with a spirochetal infection). In some embodiments of the present invention, a sample is taken from a patient and cultured. In the most preferred embodiments, at least one medium of the present invention is inoculated with the patient sample and the spirochetes allowed to grow in the culture. The expanded spirochete culture is tested in an antibiotic susceptibility test panel to identify antimicrobial agents that effectively target the patient's spirochetes. One or more of the suitable antimicrobial agents is administered to treat the patient and eliminate the disease and/or infection. Experiments conducted during the development of the present invention have demonstrated great success in human subjects. For example, patients exhibiting symptoms of multiple sclerosis and Lyme disease were individually tested for spirochete susceptibility and treated with an antibiotic cocktail specifically designed for their infection. Undesired symptoms of the diseases were successfully ameliorated. However, in other embodiments, an antimicrobial or antimicrobial cocktail shown to be effective by the methods of the present invention is directly administered to the patient without conducting a susceptibility analysis for the specific patient.

The methods and compositions of the present invention thus provide dramatic new systems for culturing spirochetes, identifying spirochete infections or contamination, identifying disease states associated with spirochete infection, and effectively treating patients having a spirochete infection. For example, the present invention has demonstrated a link between spirochete infection and patients diagnosed with diseases such as multiple sclerosis (a disease that affects over one million people and has no known cure). The methods and compositions of the present invention have been used to dramatically improve the conditions of such patients.

DEFINITIONS

To facilitate an understanding of the present invention, a number of terms and phrases are defined below:

As used herein, the terms "microbiological media" and "culture media," and "media" refer to any substrate for the maintenance, growth, and reproduction of microorganisms. "Media" may be used in reference to solid plated media which support the growth of microorganisms. Also included within this definition are semi-solid and liquid microbial growth systems including those incorporating living host organisms, as well as any type of media.

As used herein, the term "host" refers to any animal including insects and warm blooded mammals. Warm blooded mammals include, but are not limited to, humans, non-human primates, rodents, and the like, which is to be the recipient of a particular treatment. Typically, the terms "host" and "patient" are used interchangeably herein in reference to a human or mammalian subject.

As used herein, the term "non-human animals" refers to all non-human animals. Such non-human animals include, but are not limited to, vertebrates such as rodents, non-human primates, ovines, bovines, ruminants, lagomorphs, porcines, caprines, equines, canines, felines, ayes, etc.

As used herein, the term "mycoplasma" refers to members of the family Mycoplasmataceae—highly pleomorphic, gram-negative, aerobic to facultatively anaerobic microorganisms differing from bacteria in that they lack a cell wall and are bounded by a triple-layered membrane. Mycoplasma are the smallest known free-living organisms, and include the pleuropneumonia-like organisms (PPLO), and are separated into species on the basis of source, glucose fermentation, and the growth on agar media.

The terms "sample" and "specimen" in the present specification and claims are used in their broadest sense. On the one hand they are meant to include a specimen or culture. On the other hand, they are meant to include both biological and environmental samples. These terms encompasses all types of samples obtained from humans and other animals, including but not limited to, body fluids such as urine, blood, fecal matter, cerebrospinal fluid (CSF), semen, and saliva, as well as solid tissue. These terms also refers to swabs and other sampling devices which are commonly used to obtain samples for culture of microorganisms.

Biological samples may be animal, including human, fluid or tissue, food products and ingredients such as dairy items, vegetables, meat and meat by-products, and waste. Environmental samples include environmental material such as surface matter, soil, water and industrial samples, as well as samples obtained from food and dairy processing instruments, apparatus, equipment, disposable and non-disposable items. These examples are not to be construed as limiting the sample types applicable to the present invention.

DETAILED DESCRIPTION OF THE INVENTION

The present invention provides compositions and methods for the growth, detection, and antimicrobial testing of spirochetes and provides compositions and methods for the treatment of samples and patients infected with spirochetes. Certain preferred embodiments of the present invention are described in detail below. The present invention is not limited to these particular described embodiments. The description is provided in the following section: I) Culture media; II) Spirochete detection; III) Antimicrobial susceptibility testing; IV) Antimicrobials and antimicrobial cocktails; V) Treatment of infected samples and patients; and VI. Therapeutic Preparations And Combinations.

I) Culture Media

The present invention provides media for culturing spirochete organisms. The media of the present invention is the only media available that will culture all spirochete species in vitro, including the Treponemes. In preferred embodiments of the present invention, the media is serum-free. Standard currently available media for culturing certain spirochete species contain serum and do not efficiently and reliably grow the organisms. They are particularly inefficient and unreliable at growing species and strains different from those they were optimized for. Because the variability inherent in the variety of spirochete organisms, this limitation is substantial. For example, experiments conducted during the development of the present invention included testing of various formulae of media of the present invention against BSK-H media for the growth of *Borrelia* species using serum samples obtained from patients diagnosed with Lyme disease. BSK-H, a media optimized for a specific strain of *Borrelia*, failed to culture and detect spirochete in approximately 50% of the samples detected using media of the present invention.

The media of the presently claimed invention contain the nutrients needed for the metabolism and growth of spirochetes, including but not limited to carbohydrate, salt, nitrogen, metallic cation, growth factors, neural component, amino acid, and lipid sources. In preferred embodiments, the media is serum-free media. One skilled in the art will appreciate that various analogues, conjugates, complexes and the like may be substituted for the ingredients recited herein without departing from the spirit of the invention.

In preferred embodiments the source of carbohydrates includes glucose, sucrose, fructose, lactose, and mannose. While other carbohydrates may also be included, the above carbohydrates are sufficient for the growth of spirochetes using the media of the present invention. In preferred embodiments the carbohydrates are provided as (+/−10%): 1.25 g/L glucose, 1 g/L sucrose, 1.3 g/L fructose, 1.25 g/L lactose, and 1.2 g/L mannose.

In preferred embodiments the source of salts includes sodium chloride, potassium chloride, lithium chloride, calcium chloride ($2H_2O$), magnesium sulfate (anhydrous), potassium phosphate (monobasic anhydrous), and sodium phosphate (dibasic anhydrous). While other salts may also be included, the above salts are sufficient for the growth of spirochetes using the media of the present invention. In preferred embodiments the salts are provided as (+/−10%): 9 g/L sodium chloride, 1.8 g/L potassium chloride, 0.5 g/L lithium chloride, 0.185 g/L calcium chloride ($2H_2O$), 0.100 g/L magnesium sulfate (anhydrous), 0.060 g/L potassium phosphate (monobasic anhydrous), and 0.05 g/L sodium phosphate (dibasic anhydrous).

In preferred embodiments, the source of nitrogen includes peptone and neopeptone. While other sources of nitrogen may also be included, the above sources are sufficient for the growth media of the present invention. In preferred embodiments, the sources of nitrogen are provided as (+/−10%): 2.22 g/L peptone and 1.998 g/L neopeptone.

In preferred embodiments, the media of the present invention include metallic cations; in particularly preferred embodiments, the metallic cations are manganese and magnesium. While other metallic cations may also be included, the above metallic cations are sufficient for the growth of spirochetes using the media of the present invention. In preferred embodiments, the metallic cations are provided as (+/−10%): 0.052 g/L manganese and 0.044 g/L magnesium.

In preferred embodiments, the source of growth factor includes insulin components. While other growth factors may also be included, insulin components are sufficient for the growth of spirochetes using the media of the present invention. In some embodiments, factors that stimulate the insulin receptor and/or factors that initiate an insulin-like signal transduction cascade may be employed. In preferred embodiments, the insulin components are provided as 0.500 ml/L SITE+3 liquid media supplement and 0.250 ml/L N 1 medium supplement.

In preferred embodiments, the source of neural components include brain extract type 1, brain extract type 6, and sphingomyelin (Sigma). While other sources of neural components may also be included, the above sources are sufficient for the growth media of the present invention. In preferred embodiments, the sources of neural components are provided as: 0.025 g/L brain extract type 1, 0.300 g/L brain extract type 6, and 0.053 g/L sphingomyelin.

In preferred embodiments, the source of amino acids includes RPMI 1604 (50×), MEM essential amino acids, and MEM non-essential amino acids (Sigma). While other sources of amino acids may be included or substituted, the above sources are sufficient for the growth media of the present invention. In preferred embodiments, the sources of amino acids are provided as: 1 ml/L RPMI 1604 (50×), 10 g/L MEM essential amino acids, and 10 ml/L MEM non-essential amino acids.

In preferred embodiments, the source of lipids includes concentrated lipid solution (1000×) (Sigma). While other sources of lipids may be included or substituted, the above source is sufficient for the growth media of the present invention. In preferred embodiments, the concentrated lipid solution (1000×) is provided at 0.100 ml/L.

In preferred embodiments, the media further comprises insect media components. For example, in certain embodiments of the present invention the media comprises pluronic F-68 (10%) solution and Vanderzandt's supplement. In preferred embodiments, the pluronic F-68 (10%) solution is provided at 2 ml/L and the Vanderzandt's supplement is provided at 0.530 g/L (+/−10%).

In preferred embodiments, the media further comprises propellant components. For example, in certain embodiments of the present invention the media comprises L-methionine, sodium pyruvate, and L-glutamine. In preferred embodiments, the L-methionine is provided at 5 ml/L, the sodium pyruvate is provided at 22.64 g/L, and the L-glutamine is provided at 4.6 g/L (+/−10%).

In preferred embodiments, the media further comprises cell wall components. For example, in certain embodiments of the present invention the media comprises N-acetyl glucosamine. In preferred embodiments, the N-acetyl glucosamine is provided at 5 g/L.

In preferred embodiments, the media further comprises endocrine components. For example, in certain embodiments of the present invention the media comprises thyroxine, thyroid powder, and estradiol. In preferred embodiments, the thyroxine is provided at 0.12 g/L, thyroid powder at 0.22 g/L, and estradiol 0.008 g/L.

In preferred embodiments, the media further comprises additional components. For example, in certain embodiments, the present invention provides glycine, ferrous sulfate, muscle extract powder, myelin basic protein lactalbumin hydrolysate, granulated yeast, sodium bicarbonate, Hepes (all from Sigma), and brain heart infusion (Difco). In preferred embodiments, the additional components are provided as: 1.6 g/L glycine, 0.05 g/L ferrous sulfate, 0.51 g/L muscle extract powder, 0.001 g/L myelin basic protein, 10 g/L lactalbumin hydrolysate, 0.53 g/L granulated yeast, 0.05 g/L sodium bicarbonate, 5.25 g/L Hepes, and 0.66 g/L brain heart infusion.

The media of the present invention has been shown to successfully culture every type of spirochete tested, including various strains of Treponemas, Borrelias, and Leptospires. Furthermore, significant population growth of the organisms is provided by the media. In addition, any sample type may be used to inoculate the media. For example, sample such as serum, water, tissue, urine, cerebrospinal fluid, semen, amniotic fluid, fetal cord blood have been cultured successfully. Other samples, including, but not limited to lesion exudates, synovial fluid, skin, etc., may be used to inoculate the media of the present invention. However, experiments conducted during the development of the present invention demonstrated that samples (blood samples) taken from sterile tubes containing a citrate preservative or a heparinized preservative yielded little to no growth. Thus, samples placed in such preservatives should be avoided. The media of the present invention has also been shown to successfully culture *Babesia microti* and *Ehrlichia* species, tick-borne microorganisms associated with significant disease in humans and lower animals, and which may be found in conjunction with spirochetes (i.e., co-infections).

The media of the present invention are suited for use as primary culture media as well as for maintenance of spirochete cultures. For example, spirochetes may be passaged multiple times using the media of the present invention. However, it was observed during the development of the present invention that, in some embodiments, after 6 to 7 sub-passages are performed, the isolate is likely to be attenuated from its original state, typical of bacteriologic cultures grown in vitro. In some embodiments of the present invention, the media of the present invention finds use as a selective medium. For example GSI-I medium (Example 1) is a selective media as many non-spirochete species of bacterial are not grown in the medium. The medium is specific for anaerobic or microaerophilic species. Typical of these are the spirochetes other tick-born infections.

In contrast to other media currently available, the media of the present invention may be incubated at room temperature. Indeed, cultures may be maintained in the media of the present invention over a wide temperature range. For example, cultures grown at both room temperature and 37° C. have demonstrated good growth, although faster growth rates are typically obtained with the higher temperature. For example, as compared to room temperature, maintaining the incubation at 33-35° C. was shown to improve the initial growth phase of some organisms. Data also showed that incubation at 33-35° C. resulted in an increase from 0-1 organisms/field (phase microscopy) at time zero to 5-6 organisms/field within 3-4 days of incubation. Continued incubation at either the elevated or room temperature resulted in 10-12 organisms/field by 14 days of incubation. Maintaining the culture at room temperature throughout the time course requires approximately 10 extra days to reach 10-12 organisms/field.

Confirmation of growth of the desired organism, if desired, may be conducted using any number of methods. For example, successful confirmation has been achieved through immunofluorescence antibody staining, visualization by light or phase contrast microscopy, PCR amplification of spirochete-specific markers (e.g., amplification using primers encompassing a portion of the Osp A gene of *B. burgdorferi*), sequencing, and visualization by electron microscopy.

II) Spirochete Detection

The present invention provides novel methods and compositions for the detection of spirochetes. For example, the presence of spirochetes in a sample may be achieved by inoculating the media of the present invention with the sample or an aliquot of the sample. The inoculated media is incubated until a sufficient amount of organism is generated to allow their detection or characterization using the chosen method (e.g., immunofluorescence antibody staining, microscopy, PCR amplification of spirochete-specific markers, sequencing, and the like). If the sample is to be used in susceptibility testing, as described below, additional incubation may be required to achieve sufficient population of spirochete for testing.

In certain embodiment of the present invention spirochetes such as Leptospires are detected in water samples or other environmental or industrial samples suspected of containing a spirochete. For example, the media of the present invention is inoculated with a portion of the water sample and incubated until detectable levels of spirochetes are obtained. Spirochetes are detected using any of the methods described herein, or any other suitable methods. Samples containing spirochetes may undergo further characterization such as identification of particular stains of spirochete or antimicrobial susceptibility testing (described below). Samples containing spirochetes may be treated with an appropriate antimicrobial agent to remove or reduce the spirochete content, or the sample may simply be avoided (e.g., human or animal contact with the water or other contaminated substance prevented or avoided).

In other embodiments of the present invention tissues or fluid samples from a subject are tested for the presence of spirochetes. Subjects include both humans, non-human mammals (e.g., livestock), and other animals. The media of the present invention is inoculated with the sample and spirochetes are cultured and detected as described above and in the Examples. Samples infected by spirochetes may undergo further characterization such as identification of particular stains of spirochete or antimicrobial susceptibility testing (described below). Subjects infected with spirochetes may be treated with an appropriate antimicrobial agent to remove or reduce the spirochete load. Detection of spirochetes in human subject may also be used to detect, monitor, and/or prevent mother-to-child transmission of spirochete infection in utero. As shown in Example 17, the present invention describes such transmissions.

The detection methods of the present invention may also be used to identify new spirochetes (e.g., new strains and species of spirochetes and genetic variants of new or known spirochetes) and to identify the association of particular spirochetes with certain samples (e.g., water samples) or conditions (e.g., disease states). For example, use of the present invention has demonstrated an association between certain spirochete strains and human disease states such as multiple sclerosis and rheumatoid arthritis. Whether the spirochete is the direct and sole causative agent of such disease states or whether it acts to induce or exacerbates the disease state is unknown. However, such knowledge is not required for the successful practice of the present invention of the present invention, and the present invention is not limited to any particular causative mechanism of action. Rather, the present invention demonstrates and provides means to demonstrate that many patients diagnosed with such diseases, and suffering from symptoms associated with such diseases, are infected with spirochetes. Treatment with antimicrobial agents specific for the spirochete, and in some embodiments specific for a particular patient, have been shown to ameliorate the symptoms of the disease and dramatically improve patient condition. Thus, detection of spirochete infection in certain classes of patients provides novel methods and therapies for treating such patients.

The case of multiple sclerosis provides a compelling example. Experiments conducted during the development of the present invention involved testing of 146 patient samples from patients with a history of multiple sclerosis. Using media (GSI-1 media described in Example 1) and methods of the present invention, all 146 of the patients tested positive for a Leptospiral infection. Three of the 146 patients also tested positive for *Borrelia burgdorferi* infection. Interestingly, these three patients exhibited particularly severe symptoms of multiple sclerosis. Thus, the use of the present invention has resulted in the identification of a new target and provides new approaches for treating people exhibiting symptoms of multiple sclerosis. Importantly for treatment of affected individuals, current treatment regimes for multiple sclerosis do not employ any anti-bacterial agents, let alone anti-spirochetal agents or anti-spirochetal agents customized for a particular patient. For example, current research focuses on the use of intravenous immunoglobulins, plasma exchange, antiviral medications, TCR and T-cell vaccines, vitamin D therapy, bone marrow transplantation, and bee venom, among others. Most current treatments simply attempt to alleviate symptoms of the disease. Whether or not multiple sclerosis is a class of different diseases or whether many people are misdiagnosed, it is clear that a great majority of diagnosed patients are infected with spirochete that is detected and treated by the compositions and methods of the present invention.

The present invention has also found an association between rheumatoid arthritis and infection by a *Leptospira*. In view of the neurological and autoimmune conditions (See also, Lyme disease) associated with spirochete infection, it is contemplated that a variety of autoimmune and neurological diseases and patients exhibiting symptoms of autoimmune and neurological disease are infected with spirochetes, which may be detected and treated using the compositions and methods of the present invention. It is contemplated that diseases and symptoms of diseases including, but not limited to, multiple sclerosis, rheumatoid arthritis, osteoarthritis, lupus erythrematosis (both system and discoid), coronary artery disease, amyotrophic lateral sclerosis, Alzheimer's disease, chronic fatigue syndrome, ankylosing spondylitis, diabetes, hypoglycemia, depression, sleep disorders, Grave's disease, Hashimoto's disease, and Lyme disease (including gestational Lyme, neuroborreliosis, and pediatric lyme) may have a spirochetal component.

Detection methods of the present invention have successfully shown that spirochetes associated with particular disease states have consistent morphologies. For example, the leptospires found in patients diagnosed with multiple sclerosis have similar morphologies that differ from leptospires and spirochetes found in other types of patients (See, Example 11). Thus, the present invention provides novel methods for identifying particular disease states based on the morphology of the spirochete isolated from a patient. In some embodiments of the present invention, spirochetes from the patient are examined by phase contrast or electron microscopy to determine morphology. In other embodiments of the present invention, genetic signatures of spirochetes are examined and used to diagnose the disease state. For example, spirochete nucleic acid may be sequenced or used in a hybridization assays with strain-specific probes to visualize and analyze the morphology of the isolated organism.

Diagnosis of disease states may also be accomplished through the co-detection of other agents with a spirochete. For example, experiments conducted during the development of the present invention have determined that rheumatoid arthritis patients show the presence of a mycoplasma in the vicinity of or directly associated with a spirochete. Thus, the co-detection of spirochete and mycoplasma provides a indication of rheumatoid arthritis.

With respect to water samples and other environmental samples, the present invention provides efficient methods for filtering the samples to extract spirochetes. For example, in one embodiment of the present invention antibodies or other binding agents specific for a spirochete detected in a sample are fixed to a solid support (e.g., filters) and used to eliminate spirochetes from the sample (e.g., water flows in a water treatment facility).

III) Antimicrobial Susceptibility Testing

The present invention provides methods for conducting antimicrobial susceptibility testing of spirochetes. Samples containing a spirochete are cultured to obtain a sufficient amount of bacteria to allow susceptibility testing. Samples are then treated with one or more antimicrobials and growth and survival of the spirochete is examined. Such methods allow for the detection of antimicrobials that are lethal to particular spirochetes and/or classes of spirochetes.

Due to the difficulty of cultivating spirochetes among other problems (e.g., fastidious growth requirements and microaerophilic environment), prior to the present invention, easy to perform antimicrobial susceptibility tests suitable for use with all spirochetes were unavailable. However, using the methods and media of the present invention, sensitivities can be reliably and easily performed. Although, in some cases, susceptibility tests are directly performed on cultured samples (i.e., cultured using the media of the present invention), several technical problems had to be surmounted in order to allow the sensitivities of the present invention to work generally. For example, a reliable media was required. Additionally, the total number of spirochetes needed to be expanded and maximized in order to provide a sufficient number of organisms for testing. In some embodiments of the present invention, this was accomplished by centrifugation and disruption of the spirochetes. For example, in one embodiment of the present invention, spirochetes are disrupted by treatment with 10% SDS solution at 14,000 g so that the maximum number of epitopic sites are available.

The next technical hurdle was to develop methods and media to maximize the concentration of spirochetes. In one embodiment of the present invention this was accomplished by using an alternative growth medium containing an increased lactalbumin hydrolysate and brain heart infusion concentrations. In a preferred embodiment, the medium comprises one part GSI-1 medium, one part of 6.5% lactalbumin hyrdolysate, one part 2% brain heart infusion, and one part 10% pluronic fluid. The medium was inoculated with isolate and allowed to incubate in a closed sterile microcentrifuge tube until a distinctive pellet was observed.

For susceptibility testing, the organisms harvested could be assayed using any suitable susceptibility assay (See, Example 7). In some embodiments of the present invention, MICROSCAN antibiotic susceptibility plates were inoculated and incubated. Following incubations, plates were scanned for growth and respective sensitivity reaction. Each MICROSCAN plate had a positive control (growth) well and a corresponding negative control well. For the results to be considered reliable, the no growth of organisms was accepted in the negative control well, while the positive control well had to have sufficient growth to be read. In some embodiments of the present invention, to confirm the presence or absence of growing spirochetes in the growth well, aliquots from the growth well were reinoculated with fresh growth media and after an incubation time (e.g., 7-10 days) the presence of the organisms was confirmed (e.g., by phase contrast microscopy or direct fluorescent antibody staining).

In some embodiments of the present invention susceptibility assays are conducted on samples suspected of containing a spirochete to determine specific antimicrobial agents capable of killing or inhibiting the specific spirochete present in the sample. Because of the variability in spirochete species and strains, such methods are desired in order to select effective treatments. For example, antimicrobial susceptibility assays provide a determination of the appropriate antimicrobial treatment to be used originally in an infected patient. In addition, these methods provide means to monitor the efficacy of the treatment. Such determinations are useful to detect and counter any resistance that develops in the patient's culture. For example, for long term therapies (e.g., treatment over a period of years), repeated susceptibility testing is desired to optimize ongoing treatments as particular antimicrobials become less effective.

In other embodiments of the present invention susceptibility assays are conducted to determine specific antimicrobials, classes of antimicrobials, and/or antimicrobial cocktails that may be used generally (e.g., against a certain genus, species, or strain of spirochete). For example, in some embodiments of the present invention, samples from a suitable number of patients with a particular disease or spirochetal infection are obtained and assayed. Antimicrobials that effectively target a high percentage of the patients are identified. These high percentage antimicrobials are then used to treat patients having the particular disease or spirochetal infection. In some embodiments of the present invention, two or more of the antimicrobials that collectively treat a high percentage of patients are identified. In such embodiments, individual antimicrobials may only affect a portion of the population, but the collective effect of the combination provides the desired certainty. In preferred embodiments of the present invention, 80% or more of the spirochete samples tested are susceptible to the antimicrobial or combination. In particularly preferred embodiments, 90%, 95%, 98%, 99%, or 99.5% of spirochete samples are susceptible. In preferred embodiments, the total number of antimicrobials used to achieve the desired susceptibility rate is minimized and in particularly preferred embodiments the total number is three or less.

IV) Antimicrobials and Antimicrobial Cocktails

The present invention provides antimicrobials and antimicrobial cocktails that are useful in the treatment of spirochetal disease and infection. As described above, the identity of antimicrobials and antimicrobial cocktails that are effective for a particular disease or spirochete may be determined using the susceptibility assays of the present invention. The present invention contemplates that any antimicrobial may find use with the present invention. Any agent that can kill, inhibit, or otherwise attenuate the function of spirochete may be used, as well as any agent contemplated to have such activities. Antimicrobial agents include, but are not limited to, natural and synthetic antibiotics, antibodies, inhibitory proteins, anti-sense nucleic acids, membrane disruptive agents and the like, used alone or in combination.

Indeed, any type of antibiotic may be used including, but not limited to, anti-bacterial agents, anti-viral agents, anti-fungal agents, and the like. In preferred embodiments the antimicrobial of the present invention is an antibiotic. The present invention is not limited to any particular type of antibiotic. Antibiotics that find use in the present invention include, but are not limited to, Acyclovir (Zovirax), Amantadine (Symmetrel), Amikacin (generic), Gentamicin, Tobramycin, Amoxicillin, Amoxicillin/Clavulanate (Augmentin), Amphotericin B (Fungizone), Ampicillin, Ampicillin/sulbactam (Unasyn), Atovaquone (Mepron), Azithromycin (Zithromax), Cefazolin, Cefepime (Maxipime), Cefotaxime (Claforan), Cefotetan (Cefotan), Cefpodoxime (Vantin), Ceftazidime, Ceftizoxime (Cefizox), Ceftriaxone (Rocephin), Cefuroxime (Zinacef), Cephalexin, Chloramphenicol, Clotrimazole (Mycelex), Ciprofloxacin (Cipro), Clarithromycin (Biaxin), Clindamycin (Cleocin), Dicloxacillin, Doxycycline, Erythromycin (including estolate, ethylsuccinate, gluceptate, lactobionate, and stearate), Famciclovir (Famvir), Fluconazole (Diflucan), Foscarnet (Foscavir), Ganciclovir (Cytovene), Imipenem/Cilastatin (Primaxin), Isoniazid, Itraconazole (Sporanox), Ketoconazole, Metronidazole (Flagyl), Nafcillin, Nitrofurantoin, Nystatin, Penicillin (including G benzathine, G potassium, G procaine, V potassium), Pentamidine, Piperacillin/Tazobactam (Zosyn), Rifampin (Rifadin), Ticarcillin/Clavulanate, Trimethoprim, Trimethoprim Sulfate, Valacyclovir (Valtrex), Vancomycin, Aztreonam, Levofloxacin (Levaquin), Meropenem, Tobramycin, Cephalothin (Tazidime), Mezlocillin, Nalidixic acid, Netilmicin, Minocycline, Ofloxacin, Norfloxacin, Sulfamethoxazole, Tetracycline, Neomycin, Streptomycin, Cephalosporin, Ticarcillin, carbenicillin, cloxacillin, Cefoxitin, ceforanide, teicoplanin, ristocetin, viomycin, capreomycin, bacitracin, gramicidin, gramicidin S, tyrocidine, Tachyplesin, kanamycin, methicillin, oxacillin, azocillin, bacampicillin, carbenicillin indanyl, cephapirin, cefaxolin, cephradine, cefradoxil, cefamandole, cefaclor, cefuromime axetil, cefonicid, cefoperazone, demeclocytetracycline, methacycline, oxytetracycline, spectinomycin, ethambutol, aminosalicylic acid, pyrazinamide, ethionamide, cycloserine, dapsone, sulfoxone sodium, clofazimine, sulfanilamide, sulfacetamide, sulfadiazine, sulfixoxazole, cinoxacin, methenamine, and phenazopyridine. The present invention contemplate that any other antibiotic now known or discovered in the future may be used in the methods and compositions of the present invention (e.g., may be used in susceptibility assay to determine ability to treat spirochetal infections).

Experiments conducted during the development of the present invention identified a variety of antibiotic and antibiotic cocktails that find particular use in treating spirochetal infections. For example, the results of several hundred patient samples having *Borrelia* and *Leptospira* infections were tested using the susceptibility methods of the present invention. The results are present in Example 8. As is clear from this data, there are a variety of antibiotics and antibiotic combinations that achieve very high success rates. However, individual patients may not respond to any particular high percentage antibiotic. For example, as shown in Example 7, a susceptibility profile from a specific human patient showed resistance to augmentin, an antibiotic with over 80% effectiveness in the population, but was sensitive to aztreonam, an antibiotic with less than 20% effectiveness in the population. Thus, in some embodiments of the present invention, a susceptibility assay is performed on cultures from individuals to determine the appropriate antibiotic treatment or, in the alternative, a antibiotic cocktail is used. Preferably, the cocktail contains only two or three high percentage antibiotics to minimize unnecessary overuse of antibiotics, selection for broad spectrum resistance, and unwanted side-effects, while maximizing likelihood of success (i.e., as opposed to using a shot-gun approach).

Experiments conducted during the development of the present invention have identified certain specific antibiotic cocktails that are particularly efficacious. In preferred embodiments of the present invention the antibiotic cocktail comprises a tetracycline antibiotic (e.g., demeclocytetracycline, doxycycline, methacycline, minocycline, and oxytetracycline). In particularly preferred embodiments, the tetracycline antibiotic is doxycycline or minocycline. In preferred embodiment the cocktail further comprises a quinalone (e.g., nalidixic acid, cinoxacin, norfloxacin, gentamicin, azithromycin, clarithromycin, levofloxacin, ofloxacin, and ciprofloxacin, preferably ciprofloxacin), a macrolide, and/or a beta-lactam (e.g., amoxicillin and augmentin). In other embodiments, the cocktail comprises a tetracycline and a aminoglycoside (e.g., amikacin, gentamicin C, kanamycin A, neomycin B, netilmicin, streptomycin, and tobramycin) and/or a cephalosporin (e.g., cephapirin, cefaxolin, cephalexin, cephradine, cefadroxil, cefamandole, cefoxitin, cefaclor, cefuroxime, cefuroxime axetil, cefonicid, cefotetan, ceforanide, cefotaxime, ceftizoxime, ceftriaxone, cefoperazone, and ceftazidime). Other combination that find use in certain embodiments of the present invention include ampicillin/solbactam, ticarcillin/clavulanate, piperacillin/tazobactam, amoxicillin/clavulanate, and trimethoprim/sulfamethoxazole.

V) Treatment of Infected Samples and Subjects

The present invention provides methods and composition for the treatment of infected materials (e.g., water sources and food sources) and subjects (e.g., humans, as well as, other animals) infected with a spirochete. As described above, the present invention provides methods and compositions for the detection of spirochetal infections and methods and compositions for the identification of antimicrobials effective at reducing or eliminating the infections. Thus, the present invention provides all of the steps necessary for diagnosing spirochete infection and provides appropriate treatments. In some embodiments of the present invention, detection is not required prior to treatment. For example, samples suspected of containing a spirochete or subjects having symptoms consistent with a spirochete infection (e.g., neurological and autoimmune symptoms) or having a disease diagnosis associated with a spirochetal infection are directly treated with antimicrobials (e.g., antimicrobial cocktails developed by the methods of the present invention to be statistically likely to treat a spirochete infection) without first detecting the presence of a spirochete (i.e., the patients are treated empirically using knowledge gained by the practice of the present invention).

The antimicrobial treatments of the present invention can be administered by any number of routes and in any number of forms. For example, the treatments may be administered by routes including, but not limited to, orally, topically, rectally, vaginally, by pulmonary route (e.g., by use of an aerosol), or parenterally, including, but not limited to, intramuscularly, subcutaneously, intraperitoneally, intracranially, intrathecally, or intravenously. The compositions can be administered alone, or can be combined with a pharmaceutically-acceptable carrier, adjuvant, or excipient according to standard pharmaceutical practice.

In embodiments where the subject is treated for neurological symptoms or where the spirochete is suspected to be in neural tissues, the treatments of the present invention may be modified or utilized in methods that promote activity across the blood-brain barrier. The blood-brain barrier is a capillary barrier comprising a continuous layer of tightly bound endothelial cells. These cells permit a low degree of transendothelial transport, and exclude molecules in the blood from entering the brain on the basis of molecular weight and lipid solubility.

In one embodiment of the present invention, the treatment compositions of the present invention are conjugated to carrier molecules that assist the compounds of in traversing of the brain-blood barrier (See e.g., U.S. Pat. Nos. 4,540,564, 4,771,059, 4,824,850, and 5,296,483, all of which are herein incorporated by reference in their entireties). In other embodiments, the treatment compositions of the present invention are administered to a subject that has been subjected to one or a combination of techniques that increase the permeability of patient's blood-brain barrier to therapeutic compounds. An example of such a method is described in U.S. Pat. No. 5,752,515, herein incorporated by reference in its entirety. In still further embodiments, compounds known to increase the permeability of the blood-brain barrier are co-administered with the treatment compositions of the present invention. Example of such compounds are described in U.S. Pat. Nos. 5,112,596, 5,154,924, 5,268,164, 5,506,206, and 5,686,416, all of which are herein incorporated by reference in their entireties. In yet other embodiments the treatment compositions of the present invention are delivered to a patient at predetermined sites directly into the brain or neural tissue. For example, U.S. Pat. No. 5,792,110 (incorporated herein by reference in its entirety) teaches a delivery system for therapeutic agents that includes a guide cannula for penetrating a selected site in a subject to a predetermined depth and a delivery cannula for delivering the therapeutic agent to the subject. The ability of certain delivery systems to provide efficacious delivery of particular treatment compositions can be tested using artificial in vitro blood-brain barrier models (See e.g., U.S. Pat. No. 5,260,210, herein incorporated by reference in its entirety).

VI. Therapeutic Preparations And Combinations

In some embodiments, the present invention provides therapeutic compositions of antimicrobials or antimicrobial cocktails (as described in Section IV), and pharmaceutical agents typically used to treat diseases such as Lyme disease, rheumatoid arthritis, leptospirosis, etc (e.g., leflunomide, etanercept, and infliximab for rheumatoid arthritis). This combination therapy may further be combined with molecules used to assist traversal of the blood brain barrier. It is not intended that the present invention be limited by the particular nature of the therapeutic composition. For example, such compositions can be provided together with physiologically tolerable liquids, gels, solid carriers, diluents, adjuvants and excipients (and combinations thereof). Suitable pharmaceutical agents that may be combined with the antimicrobials of the present invention include, but are not limited to salicylate, steroids, immunosuppressants, or antibodies.

The therapeutic compositions of the present invention can be administered to non-human animals (e.g., for veterinary use), such as with domestic animals (e.g., livestock and companion animals), wild animals, and non-human primates, and clinical use in humans in a manner similar to other therapeutic agents. In general, the dosage required for therapeutic efficacy varies according to the type of use and mode of administration, as well as the particularized requirements of individual hosts. The attending medical professional is capable of determining the therapeutically effective dosage based on the characteristics of the subject.

Therapeutic compositions may contain such normally employed additives as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions typically contain 1%-95% of active ingredient, preferably 2%-70%.

The therapeutic compositions of the present invention can also be mixed with diluents or excipients which are compatible and physiologically tolerable. Suitable diluents and excipients are, for example, water, saline, dextrose, glycerol, or the like, and combinations thereof. In addition, if desired, the compositions may contain minor amounts of auxiliary substances such as wetting or emulsifying agents, stabilizing or pH buffering agents.

In some embodiments, the therapeutic compositions of the present invention are prepared either as liquid solutions or suspensions, as sprays, or in solid forms. Oral formulations usually include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%-95% of active ingredient, preferably 2%-70%. One example of an oral composition useful for delivering the therapeutic compositions of the present invention is described in U.S. Pat. No. 5,643,602, incorporated herein by reference in its entirety.

Additional formulations which are suitable for other modes of administration, such as topical administration, include salves, tinctures, creams, lotions, transdermal patches, and suppositories. For salves and creams, traditional binders, carriers and excipients may include, for example, polyalkylene glycols or triglycerides. One example of a topical delivery method is described in U.S. Pat. No. 5,834,016, incorporated herein by reference in its entirety. Other liposomal delivery methods may also be employed. In certain embodiments, the therapeutic compositions are administered via a transdermal patch (See e.g., U.S. Pat. Nos. 4,638,043, 5,830,505, and 5,876,746, all of which are incorporated herein by reference in their entireties).

In other preferred embodiments, enteric formulations are employed. The covering may comprise an enteric coating or a capsule. The terms "enteric coating" or "enteric film" are used interchangeably and refer to a material or compound that is resistant to acid pH (i.e., an acid-resistant compound), such as that found in the stomach. An enteric coating when applied to a solid inhibits the dissolution of the solid in the stomach.

Standard techniques may be employed for the encapsulation of solid compositions. These techniques include microencapsulation of a solid composition wherein an enteric coating is applied to the solid composition. The coated material may be delivered orally to a subject by suspending the microencapsulated particles in pharmaceutical suspension solutions. The capsule preferably has the characteristic of being resistant to dissolution in the stomach and being capable of dissolving in the intestines. Numerous suitable capsule formulations are known; in addition standard techniques are available for the filling of capsules including the use of inert filler materials to provide sufficient bulk of the filling of a capsule with a therapeutic composition in a solid form. In addition to the use of encapsulated compositions, the antimicrobial therapeutic compositions of the present invention may be delivered orally in tablet or pill form. The therapeutic compositions of the present invention may be combined with inert materials to provide sufficient bulk for the pressing of the tablet or pill. Once formed, the tablet or pill may then be coated with an enteric film to prevent dissolution in the stomach and to enhance dissolution in the intestines.

EXPERIMENTAL

The following examples serve to illustrate certain preferred embodiments and aspects of the present invention and are not to be construed as limiting the scope thereof.

In the experimental disclosure which follows, the following abbreviations apply: N (normal); M (molar); mM (millimolar); μM (micromolar); mol (moles); mmol millimoles); μmol (micromoles); nmol (nanomoles); pmol (picomoles); g grams); mg (milligrams); μg (micrograms); ng (nanograms); l or L (liters); ml milliliters); μl (microliters); cm (centimeters); mm (millimeters); μm (micrometers); nm (nanometers); ° C. (degrees Centigrade); and Sigma (Sigma Chemical Co., St. Louis, Mo.).

Example 1

Preparation of GSI-1 Spirochete Culture Medium

This Example describes the preparation of a one liter sample of the GSI-1 type Spirochete culture medium of the present invention. The various components used to make the media and their respective concentrations are listed below in Table 1.

TABLE 1

Components Used to Make 1 Liter of GSI-I Medium

| Category | Component | Amount |
| --- | --- | --- |
| Sugars (Sigma) | Glucose | 1.250 g/L |
| | Sucrose | 1.000 g/L |
| | Fructose | 1.300 g/L |
| | Lactose | 1.250 g/L |
| | Mannose | 1.200 g/L |
| Salts (Sigma) | Sodium Chloride | 9.000 g/L |
| | Potassium Chloride | 1.800 g/L |
| | Lithium Chloride | 0.500 g/L |
| | Calcium Chloride-2H$_2$O | 0.185 g/L |
| | Magnesium Sulfate (anhydrous) | 0.100 g/L |
| | Potassium Phosphate monobasic (anhydrous) | 0.060 g/L |
| | Sodium Phosphate Dibasic (anhydrous) | 0.050 g/L |
| Nitrogen (Difco) | Peptone | 2.220 g/L |
| | Neopeptone | 1.998 g/L |
| Metallic Cations (Sigma) | Manganese | 0.052 g/L |
| | Magnesium | 0.044 g/L |
| Insulin Components (Sigma) | SITE + 3 Liquid Media Supplement | 0.500 ml/L |
| Amino Acids (Sigma) | N 1 Medium Supplement | 0.250 ml/L |
| | RPMI 1640 (50 X) | 1.000 ml/L |
| | MEM Essential Amino Acids | 10.000 g/L |
| | MEM Non-Essential Amino Acids | 10.000 ml/L |
| Insect Media Components (Sigma) | Pluronic F-68 (10%) Solution | 2.000 ml/L |
| | Vanderzandt's Supplement | 0.530 g/L |
| Propellant Components (Sigma) | L-Methionine | 5.000 ml/L |
| | Sodium Pyruvate | 22.640 g/L |
| | L-Glutamine | 4.600 g/L |
| Neural Components (Sigma) | Brain Extract Type 1 | 0.025 g/L |
| | Brain Extract Type 6 | 0.300 g/L |
| | Sphingomyelin | 0.053 g/L |
| Lipids (Sigma) | Concentrated Lipid Solution (1000 X) | 0.100 ml/L |
| Cell Wall Component (Sigma) | N-Acetyl Glucosamine | 5.000 g/L |
| Endocrine Components (Sigma) | Thyroxine | 0.120 g/L |
| | Thyroid Powder | 0.220 g/L |
| | Estradiol | 0.008 g/L |
| Other Components (Sigma) | Glycine | 1.600 g/L |
| | Ferrous Sulfate | 0.050 g/L |
| | Muscle Extract Powder | 0.510 g/L |
| | Myelin Basic Protein | 0.001 g/L |
| | Lactalbumin Hydrolysate | 10.00 g/L |
| | Granulated Yeast | 0.530 g/L |
| | Sodium Bicarbonate | 0.050 g/L |
| | Brain Heart Infusion (Difco) | 0.660 g/L |
| | Hepes | 5.250 g/L |

The preparation of the GSI-1 media begins with approximately 400-500 mL of sterile water (for irrigation) poured into a sterile, gamma irradiated plastic disposable receiver. A sterilized plastic magnetic stirring bar is placed into the receiver and the assembly is placed on a non-heated magnetic stirring plate.

The solid components from Table 1 are added one at a time in any order, and allowed to mix for several hours at ambient room temperature. After thorough mixing has been achieved, the assembly and the mixed components are placed inside an operating Class II Laminar Flow Hood where the liquid components are added one at a time using aseptic tissue culture technique. The final volume of 1.00 Liter is achieved by adding additional sterile water for irrigation. The combined mixture is allowed to stir for another hour, and then vacuum filtrated into a sterile, gamma irradiated plastic receiver through a 0.22 micron cellulose acetate membrane filter.

After the medium is prepared, it is tested for sterility. This is done by inoculating several loopfuls of new media onto a fresh 5% sheep blood agar plate and allowed to incubate overnight. If no colonies are present on the plate the next day, it is ready for use as a culture medium for spirochete microorganisms. However, if colonies are present, the process is repeated. If two consecutive blood agar plate attempts are positive for bacterial contamination, the medium is discarded. The sterile medium is stored at 4° C. until use.

Example 2

Inoculating GSI-I Medium with a Sample

This examples describes inoculating GSI-1 medium with a sample in order to culture spirochetes. To culture microorganisms on GSI-I, 80% media is used for a 20% amount of inoculum (whether it be water or body fluids like serum, urine, cerebrospinal fluid, synovial fluid, semen, amniotic fluid, or fetal cord blood). In this example, a sterile flask is assembled within a class II laminar flow hood along with the refrigerated GSI-1 culture medium prepared according to Example 1 and a patient serum sample in a capped test tube. The 80% volume of GSI-1 media is aseptically transferred or pipetted into the sterile flask. The media is then recapped and placed back into the refrigerator for storage. The test tube with the patient serum sample is then uncapped, and the 20% of serum is aseptically placed within the sterile flask containing sterile GSI-1 media. The flask is then capped to ensure a microaerophilic growth environment and incubated at room temperature until microscopic examination is performed. At various time periods the inoculated culture sample is examined. Examination includes both visual identification under a microscope and an antibody binding screen.

The GSI-1 culture media was also used to culture organisms present in tissue samples. For example a cryopreserved biopsy material from a tick bite rash (i.e., erythema migrans) from a Lyme disease patient was cultured in the GSI-1 media. The tissue sample was approximately 2 by 4 by 4 millimeters in volume. GSI-1 media was transferred to the sterile flasks. The cyropreserved erythema migrans biopsy sample was then transferred into the sterile flask. The flask was then capped and incubated until microscopic examination was performed. At various time periods, the inoculated culture samples are examined. Examination includes methods such as visual identification under a microscope, an antibody binding screen, and PCR analysis.

Example 3

Use of GSI-1 Media to Screen for Spirochetes

This example describes screening of inoculated GSI-1 medium for the presence of *Treponema*, *Borrelia*, and *Leptospira*. Five serum samples previously confirmed by assay for RPR (rapid plasma reagin) and MHA-TP (microhemagglutination assay for *T. pallidum*) were used in these experiments. Each of the five samples were inoculated in GSI-1 (e.g., in the manner described in Example 2). At inoculation, less than one organism per field was observed by phase contrast microscopy in these culture samples. The cultures were allowed to grow for 21 days at 37° C. Each of the cultures was then assayed using *T. pallidum* specific indirect and direct immunofluorescence antibody staining. Dilutions of 1:10 and 1:20 were performed with the appropriate controls (e.g., negative controls such as blanks and *Leptospira* antigen and positive controls such as a *T. pallidum* positive slide). After application, the reaction was allowed to incubate for 45 minutes at 37° C. prior to counting. Examination by fluorescent microscopy demonstrated intact, motile spirochetes in each of the five culture samples. Examination by fluorescent microscopy also revealed that the number of organisms in each culture sample had increased to approximately 10-14 organisms per field, as compared to the 0-1 organisms present at inoculation. This example makes it clear that the GSI-I media was able to effectively grow *T. pallidum* in vitro.

Screening the GSI-1 media for *Borrelia burgdorferi* was performed by the following method. Approximately 100 serum samples from clinical cases of Lyme disease were obtained. Each of the samples was inoculated in the GSI-1 media (e.g., as described in Example 2) to form a culture sample. The cultures were allowed to grow for 14 days at 37° C. Each of the cultures was then screened by phase contrast microscopy, which revealed approximately 10-12 organisms per field. At 21 days, the culture was examined by direct immunofluorescent antibody staining. Examination by fluorescent microscopy demonstrated intact, motile spirochetes in each of the samples. Examination also revealed that the number of organisms in each culture sample had increased to approximately 16-18 organisms per field. Positive results were further confirmed by PCR and dideoxy DNA sequencing (see Example 4 below). This Example makes it clear that the GSI-1 was able to effectively grow the *Borrelia burgdorferi* in vitro.

Screening the GSI-1 media for *Leptospira biflexa* was performed by the following method. Seven samples of serum from culture isolates of patients with multiple sclerosis and rheumatoid arthritis were obtained. Each of the seven samples were inoculated in GSI-1 (e.g., as described in Example 2). The cultures were allowed to grow for 14 days. Each of the cultures was then assessed using *L. biflexa* specific direct antibody staining at dilutions of 1:10, 1:20 and 1:25. The specific antibodies were allowed to incubate for 45 minutes at 37° C. prior to counting. Examination by fluorescent microscopy demonstrated distinct, motile spirochetes in each of the seven culture samples. Examination also revealed that the number of organisms had increased to approximately 14-18 organisms per field. This example makes it clear that GSI-1 media was able to effectively grow *Leptospira biflexa* in vitro.

Example 4

Analysis of a *Borrelia burgdorferi* Sample

This example describes the further analysis of a GSI-1 culture that was identified as *Borrelia burgdorferi* positive by immunofluorescent antibody staining, phase contrast microscopy, and fluorescent microscopy. In particular, PCR was carried out on this sample, and the amplified product was sequenced by the dideoxy sequencing method.

PCR was carried out employing the QIA Amp DNA kit (Qiagen). The two primers employed were: BB ASPA 56-76 5'-AAAATGTTAGCAGCCTTGACG-3' (SEQ ID NO:1) and OSPA 438-465 5'-AGATCCATCGCTTTTAATTCCTGTG-TAT-3' (SEQ ID NO:2), both from Integrated DNA Technology Inc. These primers are specific for a 410 base pair fragment of the gene encoding the outer surface protein A (Osp A) of *Borrelia burgdorferi*. The primers (each at 0.5 µl) were added to 20 µl of DNA isolated from the *B. burgdorferi* culture sample in an Eppendorf tube, along with the following reagents: 15 µl $H_2O$, 5 µl 10×PCR Gold buffer, 4 µl of 25 mM $MgCl_2$, 4 µl of a dNTP mix (2.5 mM of each dNTP), and 1 ul of Ampli Taq Gold. The reaction conditions were as follows: 94° C. for 3 minutes for one cycle, 35 cycles at 94° C./45 seconds; 48° C./60 seconds; 72° C./1 minute; final extension 72° C./5 minutes. The purified amplified PCR product was then sequenced using the CEQ 2000 DNA analysis system (Beckman). The sequencing system, which uses the dideoxy chain termination method for sequencing, was employed as directed by the manufacturer. The determined sequence (SEQ ID NO: 3) is listed in FIG. 1. Bases 1-129 of SEQ ID NO:3 were then blasted against known sequences using NCBI's Blast Search program (http://www.ncbi.nlm.nih.gov/BLAST/). Three sequences representing *Borrelia burgdorferi* Osp A protein revealed 97% identity (128/131) with this sequence: AF026059 (*B. burgdorferi* 50 kDa plasmid lipoprotein (ospA) gene, complete cds; BBT25OSPA (*B. burgdorferi* ospA gene, T255 substrain); and BBU65813 (*B. burgdorferi* strain Mho2 ospA gene, partial cds). These results confirm the presence of *B. burgdorferi* in the culture sample.

Example 5

Diagnosis of *Borrelia burgdorferi* Infection in a Patient

This Example describes the use of GSI-1 to diagnose *Borrelia burgdorferi* infection in a human patient. The human patient experienced some form of neurological distress for which his physicians could not determine the exact etiological agent(s). The treating physicians suspected viral encephalitis or neuroborreliosis, but a lumbar puncture test revealed nothing. Consequently, a serum sample from this patient was then cultured in the GSI-1 media of the present invention using the culture/testing procedures described in Examples 2 and 3. The result of this testing revealed the presence of *Borrelia burgdorferi* in the patient's sample. The patient was started on a course of ceftriaxone (Rocephin) and responded well until the medication was stopped. Subsequently, a brain biopsy was performed on the patient. PCR amplification specific for *Borrelia burgdorferi* was performed on the biopsy sample, and the amplified product was sequenced. The resulting sequence confirmed the diagnosis of *Borrelia burgdorferi* infection in the brain tissue of this patient.

Example 6

Preparation of Pellet for Antimicrobial Susceptibility Testing

This example describes the preparation of a pellet used for antimicrobial susceptibility testing of a culture sample. The procedure begins with a culture (e.g., prepared in the manner described in Example 2), where serum from a patient is inoculated in GSI-1 media and allowed to grow. In order to form pellet, an aliquot of this culture sample is placed in a microcentrifuge tube along with 10% SDS solution, and centrifuged at 14,000 g to disrupt the spirochetes and maximize the number of available eptiopic sites. The disrupted spirochetes were then cultured in an alternative growth medium made up of one part GSI-1 medium, one part 6.5% lactalbumin hydrolysate, one part 2% brain heart infusion, one part 10% pluronic fluid, and one part of the isolated (disrupted) spirochetes. This inoculated alternative growth medium was then allowed to incubate in the closed micro centrifuge tube until a distinctive pellet was observed (typically 7-14 days).

Example 7

Antimicrobial Susceptibility Testing

This example describes an antimicrobial susceptibility test performed for a human patient. The patient had previously been testing using GSI-1 medium (e.g., as described in Example 2) for the presence of any spirochetes. The cultured sample revealed the presence of *Treponema*. This culture sample was then transferred to a microcentrifuge tube, and a pellet for antimicrobial susceptibility testing was prepared as described in Example 6.

Following the observation of pellet formation, the tube was vortexed and incubated at 35° C. until a MacFarlane standard of between 8 to 12% turbidity was achieved. MICROSCAN antibiotic susceptibility microtiter plates were then inoculated with (e.g., 110 μl of) inoculum and allowed to incubate at 35° C. for 16-20 hours. The microtiter plates were then scanned for growth and respective sensitivity reaction (both the control well and the growth well). Table 2 below lists the various antimicrobials tested with this sample and whether growth of the organism was inhibited (susceptible) or whether the growth of the organism was not inhibited (resistant). The results in Table 2 demonstrate the variable susceptibility displayed by the *Treponema* isolate to various antimicrobials.

TABLE 2

Treponema Infected Patient's Antibiotic Susceptibility Results

| ANTIBIOTIC TESTED | RESULT |
| --- | --- |
| Augmentin | Resistant |
| Ampicillin/Sulbactam | Susceptible |
| Ampicillin | Susceptible |
| Aztreonam | Susceptible |
| Cefazolin | Resistant |
| Cephalothin | Susceptible |
| Ciprofloxacin | Resistant |
| Gentamicin | Resistant |
| Mezlocillin | Susceptible |
| Nalidixic Acid | N/A |
| Netilmicin | Resistant |
| Nitrofurantoin | N/A |
| Norfloxacin | N/A |
| Piperacillin | Susceptible |
| Sulfamethoxazole | N/A |
| Tetracycline | Resistant |
| Ticarcillin/Clavulanate | Susceptible |
| Ticarcillin | Susceptible |
| Tobramycin | Intermediate |
| Trimethoprim/Sulfamethoxazole | Resistant |
| Trimethoprim | N/A |
| Meropenem | Resistant |

Example 8

Antibiotic Susceptibility Testing of *Borrelia* and *Leptospira* Samples

This Example describes the results for susceptibility tests that were performed on a large number of patient samples positive for either *Borrelia* or *Leptospira*. In these experiments, several hundred patient samples were cultured on GSI-1 (e.g., as described in Example 2). These culture samples were then used to produce pellets for antimicrobial susceptibility testing as described in Example 6. The antimicrobial susceptibility tests were then carried out on each sample as described in Example 7 or by the disc diffusion method (e.g., instead of MICROSCAN) with the antimicrobials listed below in Table 3. Results with control organisms are also provided in Table 3. The results presented in Table 3 reveal the varied response of different types of spirochetes to different antibiotics.

TABLE 3

Antibiotic Susceptibility Test Results

| | \multicolumn{7}{c}{Organism} | | | | | | |
|---|---|---|---|---|---|---|---|
| | E. coli | Tatumella | Y. entero gp. | Borrelia | Leptospira | A. lwoffii | Pseudomonas |
| Total isolates | 1 | 2 | 1 | 519 | 276 | 1 | 1 |
| Amikacin | 100% | 100% | 100% | 84% | 85% | 100% | 100% |
| Augmentin | 100% | 100% | 100% | 90% | 89% | N/A | N/A |
| Ampicillin | 100% | 100% | 100% | 61% | 54% | N/A | N/A |
| Aztreonam | 100% | 0% | 0% | 11% | 15% | 100% | 100% |
| Cefepime | 100% | 0% | 100% | 49% | 54% | 100% | 100% |
| Cefotaxime | 100% | 0% | 100% | 60% | 64% | 100% | 100% |
| Ceftazidime | 100% | 0% | 100% | 36% | 41% | 100% | 100% |
| Cefuroxime | 100% | 0% | 100% | 59% | 59% | N/A | N/A |
| Ciprofloxacin | 100% | 100% | 100% | 84% | 78% | 100% | 100% |
| Gentamicin | 100% | 100% | 100% | 89% | 86% | 100% | 100% |
| Imipenem | 100% | 100% | 100% | 84% | 77% | 100% | 100% |
| Levofloxacin | 100% | 100% | 100% | 86% | 83% | 100% | 100% |
| Meropenem | 100% | 100% | 100% | 82% | 75% | 100% | 100% |
| Piperacillin/ Tazobactam | 100% | 100% | 100% | 88% | 86% | N/A | 100% |
| Piperacillin | 100% | 100% | 100% | 60% | 55% | 100% | 100% |
| Ticarcillin/ Clavulanate | 100% | 100% | 100% | 79% | 75% | 100% | 100% |
| Tobramycin | 100% | 100% | 100% | 81% | 84% | 100% | 100% |

Example 9

Susceptibility Testing of *Leptospira* Isolated from a Patient with Symptoms of Multiple Sclerosis This Example describes the results of antimicrobial susceptibility testing for a human patient displaying symptoms of multiple sclerosis. In particular, serum and urine samples from the patient were initially cultured on GSI-1 (e.g., as described in Example 2), and screened for the presence of *Leptospira* (e.g., as described in Example 3). *Leptospira* was detected in both cultures. These cultures were then used to produce pellets for antimicrobial susceptibility testing as described in Example 6. The antimicrobial susceptibility tests were then carried out on each sample with the antimicrobials and results listed below in Table 4.

TABLE 4

Antibiotic Susceptibility Results

| ANTIBIOTIC TESTED | SERUM | URINE |
|---|---|---|
| Tetracycline | Resistant | Resistant |
| Ofloxacin | N/A | N/A |
| Ampicillin/Sulbactam | N/A | N/A |
| Ampicillin | Resistant | Resistant |
| Rifampin | Resistant | Resistant |
| Clindamycin | Resistant | Resistant |
| Erythromycin | Resistant | Resistant |
| Clarithromycin | Resistant | Resistant |
| Azithromycin | Resistant | Resistant |
| Trimethoprim/Sulfamethoxazole | Susceptible | Susceptible |
| Cefuroxime | Resistant | Resistant |
| Cefotaxime | Resistant | Resistant |
| Ceftazidime | Resistant | Resistant |
| Cefpodoxime | N/A | N/A |
| Amikacin | Resistant | Resistant |
| Gentamicin | Resistant | Resistant |
| Tobramycin | Resistant | Resistant |
| Ciprofloxacin | Susceptible | Susceptible |
| Levofloxacin | Susceptible | Susceptible |
| Norfloxacin | N/A | Susceptible |
| Ampicillin | Resistant | Resistant |
| Amoxicillin/Clavulanate | Resistant | Resistant |
| Piperacillin | Resistant | Resistant |
| Piperacillin/Tazobactam | Intermediate | Intermediate |
| Ticarcillin/Clavulanate | Resistant | Resistant |
| Impenem | Resistant | Resistant |
| Meropenem | Resistant | Resistant |
| Aztreonam | Resistant | Resistant |

Example 10

Comparison of GSI-1 and BSK-H Media

This Example describes a comparison between GSI-1 of the present invention and the commercially available BSK-H. In particular, the ability of each of these media to culture spirochetes from patient samples is compared. Twenty-four patient samples were analyzed in these experiments, all of which were from patients previously diagnosed with Lyme disease.

The procedure for culturing the patient samples on GSI-1 was carried out using samples from clinically diagnosed Lyme patients as described in Example 2. The procedure for culturing the patient samples on BSK-H was carried out as recommended by the manufacturer (Sigma). Briefly, BSK-H medium flasks were inoculated with patient samples after 0.5 to 1.0 ml of human blood or serum was added to each flask. The flasks were then incubated between 33-35° C. for 3-4 days. The cultures were then observed for the presence of spirochetes. Confirmation was obtained using phase contrast microscopy and immunofluorescence antibody staining. The results of the 24 patient samples that were cultured on GSI-1 revealed that 23 cultures positive for *Borrelia*, confirming the positive diagnosis for these patients. The only negative sample was from a patient who had undergone four years of antimicrobial treatment which cleared the organism. Therefore, this sample was not expected to be positive on either media. Thus, GSI-1 was successful in culturing *Borrelia* from 100% of the samples expected to be positive.

This data is in stark contrast to the results obtained by culturing the patient samples on BSK-H, as only 11 of the 24 samples tested were positive for *Borrelia* (i.e. only 45.8%). Furthermore, of the 13 samples that were negative, 12 of these samples were shown by culture on GSI-1 to actually be positive for *Borrelia* infection (as stated above, the 13th negative sample was expected to be negative). Therefore, the BSK-H cultures had a false-negative rate of over 50% (52.2% according to these results). The GSI-1 media, therefore, provides a reliable media for culturing spirochetes.

Example 11

Multiple Sclerosis and Spirochete Infection

This Example describes the relationship between multiple sclerosis and spirochete infection. In particular, 146 human patients with a history of multiple sclerosis were tested for spirochete infection. Patient samples were collected from each patient and cultured on GSI-1 (See e.g., Example 2 above). These samples were then tested for spirochete infection (e.g., as described in Example 3). The results of this testing revealed that 146 of the 146 patient samples tested were positive for *Leptospira*. In other words, all of the patients with a history of multiple sclerosis tested for spirochete infection were found to be positive for *Leptospira* spirochetes. Also, 3 of the 146 patients were also found to be positive for *Borrelia burgdorferi* infection. These three patients that were positive for both *Leptospira* and *Borrelia burgdorferi* were found to exhibit severe symptoms associated with multiple sclerosis.

Scanning and transmission electron microscopy was performed on approximately 35 of the multiple sclerosis patient samples described above. The electron microscopy revealed that all the *Leptospira* spirochetes had a unique morphology not previously seen in other *Leptospira* species. Specifically, these *Leptospira* were shorter in length than other *Leptospira* spirochetes and tended to have a flagellar pattern characterized as having more flagella at one end than the other.

Example 12

Electron Microscopy of Rheumatoid Arthritis Patient Samples

This Example describes electron microscopy of cultivated patient samples from human patients with symptoms of rheumatoid arthritis. In particular, several *Leptospira* positive patient samples from patients with rheumatoid arthritis were examined by scanning and transmission electron microscopy. The electron microscopy revealed that all the *Leptospira* spirochetes had a unique morphology. Specifically, these *Leptospira* were longer in length than other samples and had a 'hook' structure at one end. Also, the *Leptospira* spirochetes were seen in close association with mycoplasma, a phenomenon not previously reported. Specifically, the mycoplasma bacteria were commonly seen either in physical contact with the *Leptospira*, or in close proximity to the *Leptospira*.

Example 13

Diagnosis and Treatment of a Patient with Symptoms of Rheumatoid Arthritis

This Example describes the diagnosis and treatment of a human patient with symptoms of rheumatoid arthritis. In particular, serum and urine samples from this patient were initially cultured on GSI-1 (e.g., as described in Example 2), and screened for the presence of spirochetes (e.g., as described in Example 3). *Leptospira* were detected in both samples. These cultures were then used to produce pellets for antimicrobial susceptibility testing (e.g., as described in Example 6). The antimicrobial susceptibility tests were then carried out on each sample (e.g., as described in Example 7) with the antimicrobials listed below in Table 5. The susceptibility results presented in Table 5 indicate that this patient's isolate was resistant to many antimicrobials. However, the information obtained from these assays was used to select Ciprofloxacin and Minocycline for treatment. Ciprofloxacin (500 mg TID), Minocycline (100 mg TID), and Nystatin (500,000 units QID) were administered orally on a daily basis for over 18 months without the development of resistance. After six weeks, the patient indicated a noticeable decrease in pain and an increase in range of motion and energy was observed. After 6 months of therapy, the patient experienced approximately 75-80% remission. At 18 months, cultures were still positive for spirochete, but overall numbers of organisms were very low as compared to the initial culture.

TABLE 5

Antibiotic Susceptibility Results for Patient with Symptoms of Rheumatoid Arthritis

| ANTIBIOTIC TESTED | SERUM | URINE |
|---|---|---|
| Trimethoprim Sulfate | Susceptible | Susceptible |
| Cefuroxime | Resistant | Resistant |
| Cefotaxime | Resistant | Resistant |
| Ceftazidime | Resistant | Resistant |
| Cefpodoxime | N/A | N/A |
| Amikacin | Resistant | Resistant |
| Gentamicin | Resistant | Resistant |
| Tobramycin | Resistant | Resistant |
| Ciprofloxacin | Susceptible | Susceptible |
| Levofloxacin | Susceptible | Susceptible |
| Norfloxacin | N/A | Susceptible |
| Ampicillin | Resistant | Resistant |
| Amoxicillin/Clavulanate | Susceptible | Susceptible |
| Piperacillin | Resistant | Resistant |
| Piperacillin/Tazobactam | Intermediate | Intermediate |
| Ticarcillin/Clavulanate | Resistant | Resistant |
| Imipenem | Intermediate | Intermediate |
| Meropenem | Resistant | Resistant |
| Aztreonam | Resistant | Resistant |
| Tetracycline | Resistant | Resistant |
| Ofloxacin | N/A | N/A |
| Penicillin | Resistant | Resistant |
| Ampicillin/Sulbactam | N/A | N/A |
| Rifampin | Resistant | Resistant |
| Clindamycin | Resistant | Resistant |
| Erythromycin | Resistant | Resistant |
| Clarithromycin | Resistant | Resistant |
| Azithromycin | Resistant | Resistant |

Example 14

Diagnosis and Treatment of a Patient with Symptoms of Multiple Sclerosis

This Example describes the diagnosis and treatment of a human patient with symptoms of multiple sclerosis. In particular, fluid samples from this patient were initially cultured on GSI-1 (e.g., as described in Example 2), and screened for the presence of spirochetes (e.g., as described in Example 3) which revealed the presence of *Leptospira* spirochetes. These cultures were then used to produce pellets for antimicrobial susceptibility testing (See e.g., Example 6), and antimicrobial susceptibility testing was carried out (See e.g., Example 7).

The susceptibility testing indicated the spirochete's susceptibility to Ciprofloxacin and Minocycline. Consequently, the patient was put on a course of daily treatment with both Ciprofloxacin and Minocycline.

The results of this treatment were dramatic. Before treatment, this patient had many severe symptoms of multiple sclerosis including difficulty breathing (shallow breathing), inability to speak, and limited upper extremities use. After 3 months of treatment, the patient had improved breathing, regained the ability to speak, and experienced dramatic improvement in the use of upper extremities. In general, treatments of patients with symptoms of multiple sclerosis according to the present invention have demonstrated in excess of 90% recovery over time, with approximately 30% of affected patients showing treatment failures, approximately 35% showing high recovery, and approximately 35% showing 50-60% improvement.

Example 15

Diagnosing and Treatment of a Patient Suspected of Having a Spirochetal Infection This Example describes the diagnosis and treatment of a person suspected of having a spirochetal infection. A clinical sample is taken from a person suffering from a neurological or autoimmune disease or other disease suspected of having spirochetal association. This sample is then cultured in the GSI-1 medium, as described in Example 2 and screened for spirochetal growth as described in Example 3. The patient sample is further screened in the alternative growth media (pellet) as described in Example 5, and screened for antimicrobial susceptibility as described in Example 6. A patient found to be susceptible to minocycline is treated with the following antibiotics, orally, on a daily basis: Ciprofloxacin (500 mg TID), Minocycline (100 mg TID), and Nystatin (500,000 units QID).

The response of the patient in the first 4 weeks of treatment is contemplated to be an increase in the disease symptoms due to a Jarisch-Herxheimer reaction (dexamethasone, 4 mg may be given to help reduce the reaction), with a reduction in symptoms beginning at approximately week 6 (increased mental clarity, increased energy, and better appetite). Symptoms gradually diminish over time.

Example 16

Testing Water Samples for Spirochete Contamination

This Example describes testing water samples for the presence of spirochete contamination. In particular, water samples taken from both upstream and downstream of a water purification facility were tested. The samples were cultured on GSI-1 as described in Example 2. Using the methods of Example 3, *Leptospira* were detected in both samples.

Example 17

Detection of *B. burgdorferi* in Maternal Serum, Amniotic Fluid, and Fetal Cord Blood This Example describes detection of *B. burgdorferi* in maternal serum, amniotic fluid and fetal cord blood. In particular, a mother was previously diagnosed with Lyme disease at least two years prior to pregnancy and was treated with various antimicrobials. The attending physician suspected gestational Lyme disease, and therefore collected maternal serum, amniotic fluid, and fetal cord blood. All three samples were cultured on GSI-1 as described in Example 2 and *Borrelia burgdorferi* was detected in all three samples employing the methods in Example 3. PCR amplification specific for *Borrelia burgdorferi* was performed on all three samples, and the amplified products were sequenced. All three samples were positive for *B. burgdorferi* by PCR amplification, but sequence confirmation was confirmed only for the maternal serum sample and the fetal cord blood sample.

Example 18

Formulation of Reliable Spirochete Culture Media

This Example describes screening alternative media mixtures for reliable spirochete culture media. In particular, the formulation of GSI-1 detailed in Example 1 is modified to create an alternative spirochete culture media by: (1) removing one or more the components or (2) exchanging one or more of the components for components known to serve a similar function in culture media, or (3) both removing and exchanging various media components. This alternative growth media is inoculated with a patient or water sample as described in Example 2. Standard GSI-1 media is also inoculated with the sample patient or water sample for comparison with the alternative growth spirochete culture media (i.e., as a positive control). Alternative growth media formulations able to culture spirochetes as well (or nearly as well) as GSI-1 are selected for use as reliable spirochete culture media.

We claim:

1. A composition comprising serum-free culture media, wherein said serum-free culture media provides a growth media that supports a dividing population of *Treponema* organisms in vitro under microaerophilic conditions wherein said serum-free culture media comprises:
   a) a sugar component comprising glucose, sucrose, fructose, lactose, and mannonse;
   b) a salt component comprising sodium chloride, potassium chloride, lithium chloride, calcium chloride, magnesium sulfate, potassium sulfate, sodium phosphate, ferrous sulfate, and sodium bicarbonate;
   c) a peptide component comprising peptone and neopeptone;
   d) an ionic component comprising manganese and magnesium,
   e) SITE +3 Liquid Media Supplement;
   f) N 1 Medium Supplement;
   g) RPMI medium;
   h) an amino acid component comprising essential amino acids, non-essential amino acids, L-methionine, and L-glutamine;
   i) pluronic F-68;
   j) Vanderzandt's supplement;
   k) sodium pyruvate;
   l) brain extract type 1;
   m) brain extract type 6;
   n) sphingomyelin;
   o) concentrated lipid solution;
   p) N-acetyl glucosamine;
   q) thyroxine;
   r) thyroid powder;
   s) estradiol;
   t) glycine;
   u) muscle extract powder,
   v) myelin basic protein,
   w) lactalbumin hydrolysate,
   x) granulated yeast
   y) brain heart infusion; and
   z) Hepes.

2. The composition of claim 1, further comprising a dividing population of said *Treponema* organism.

3. The composition of claim 1, wherein said *Treponema* organisms comprise *Treponema pallidum*.

4. A composition comprising serum-free culture media, wherein said culture media provides a growth media that supports a dividing population of *Treponema, Borrelia*, and *Leptospira* organisms, wherein said serum-free culture media comprises:
   a) a sugar component comprising glucose, sucrose, fructose, lactose, and mannonse;
   b) a salt component comprising sodium chloride, potassium chloride, lithium chloride, calcium chloride, magnesium sulfate, potassium sulfate, sodium phosphate, ferrous sulfate, and sodium bicarbonate;
   c) a peptide component comprising peptone and neopeptone;
   d) an ionic component comprising manganese and magnesium,
   e) SITE +3 Liquid Media Supplement;

f) N 1 Medium Supplement;
g) RPMI medium;
h) an amino acid component comprising essential amino acids, non-essential amino acids, L-methionine, and L-glutamine;
i) pluronic F-68;
j) Vanderzandt's supplement;
k) sodium pyruvate;
l) brain extract type 1;
m) brain extract type 6;
n) sphingomyelin;
o) concentrated lipid solution;
p) N-acetyl glucosamine;
q) thyroxine;
r) thyroid powder;
s) estradiol;
t) glycine;
u) muscle extract powder,
v) myelin basic protein,
w) lactalbumin hydrolysate,
x) granulated yeast
y) brain heart infusion; and
z) Hepes.

5. The composition of claim 4, further comprising a dividing population of a spirochete organism.

* * * * *